(12) United States Patent
Stoessel et al.

(10) Patent No.: US 9,937,438 B2
(45) Date of Patent: Apr. 10, 2018

(54) METHOD FOR VACUUM PURIFICATION

(71) Applicant: Merck Patent GmbH, Darmstadt (DE)

(72) Inventors: Philipp Stoessel, Frankfurt am Main (DE); Juergen Fuchs, Floerscheim (DE)

(73) Assignee: Merck Patent GmbH, Darmstadt (DE)

(*) Notice: Subject to any disclaimer, the term of this patent is extended or adjusted under 35 U.S.C. 154(b) by 60 days.

(21) Appl. No.: 14/911,036

(22) PCT Filed: Jul. 11, 2014

(86) PCT No.: PCT/EP2014/001911
§ 371 (c)(1),
(2) Date: Feb. 9, 2016

(87) PCT Pub. No.: WO2015/022043
PCT Pub. Date: Feb. 19, 2015

(65) Prior Publication Data
US 2016/0175736 A1    Jun. 23, 2016

(30) Foreign Application Priority Data
Aug. 13, 2013 (EP) .................................... 13004019

(51) Int. Cl.
*B01D 7/00* (2006.01)
*B01D 3/08* (2006.01)
*C07B 63/00* (2006.01)

(52) U.S. Cl.
CPC ............... *B01D 7/00* (2013.01); *B01D 3/085* (2013.01); *C07B 63/00* (2013.01)

(58) Field of Classification Search
CPC .. B01D 7/00; B01D 3/085; B01D 7/02; C07B 63/00
USPC ........................................................ 23/294 R
See application file for complete search history.

(56) References Cited

U.S. PATENT DOCUMENTS

| 4,389,794 A | 6/1983 | Bitterly |
| 5,243,836 A | 9/1993 | Spring |
| 6,666,457 B2 | 12/2003 | Genser |
| 6,878,183 B2 | 4/2005 | Soeda et al. |

FOREIGN PATENT DOCUMENTS

| CN | 1419466 A | 5/2003 |
| CN | 1714061 A | 12/2005 |
| DE | 1130793 B | 6/1962 |
| DE | 4213430 A1 | 1/1993 |
| DE | 10038986 A1 | 2/2002 |
| EP | 0504099 A1 | 9/1992 |
| WO | WO-93/00974 A1 | 1/1993 |
| WO | WO-03051796 A1 | 6/2003 |

OTHER PUBLICATIONS

International Search Report for PCT/EP2014/001911 dated Oct. 10, 2014.

*Primary Examiner* — Edward Johnson
(74) *Attorney, Agent, or Firm* — Drinker Biddle & Reath LLP (57) ABSTRACT

The present invention relates to a process for the vacuum purification of chemical compounds and to an apparatus for carrying out this process.

8 Claims, 7 Drawing Sheets

Figure 1: Apparatus for carrying out the process according to the invention

Figure 2. Apparatus with carrier-gas feed

Figure 3: Apparatus for semi-continuous work

Figure 4: Apparatus for carrying out the process according to the invention with a plurality of heating zones Figure 6: Suitable vessel shapes for sublimer and condensation units which are permanently connected

A: cylinder-cylinder

B: sphere-sphere

C: cylinder-sphere

D: cylinder-cylinder with carrier-gas feed or for semi-continuous work

Figure 7: Suitable vessel shapes for sublimer and condensation units which are not permanently connected

A: sublimer and condensation units for condensation in the liquid state

B: condensation unit for condensation in the solid state (plan view)

C: condensation unit for condensation in the solid state (side view)

METHOD FOR VACUUM PURIFICATION

CROSS-REFERENCE TO RELATED APPLICATIONS

This application is a national stage application (under 35 U.S.C. § 371) of PCT/EP2014/001911, filed Jul. 11, 2014, which claims benefit of European Application No. 13004019.9, filed Aug. 13, 2013, both of which are incorporated herein by reference in their entirety.

The present invention relates to a process for the vacuum purification of chemical compounds and to an apparatus for carrying out this process.

High-value organic, organometallic and inorganic compounds are used in a variety of applications. Thus, for example, APIs ("active pharmaceutical ingredients") are active components for pharmaceutical applications. A further important area of application are materials for electronic applications, in particular in the area of organic electronics, in which, in particular, organic semiconductors and organic conductors are used. Thus, for example, organic electroluminescent devices (OLEDs), organic solar cells (O-SCs), organic thin-film transistors (O-TFTs), organic field-effect transistors (O-FETs), organic integrated circuits (O-ICs), organic photodiodes and organic laser diodes (O-lasers) may be mentioned in the area of organic electronics.

All these applications have the following in common: in general, small amounts of material are used in order to achieve the desired effects. On the other hand, high demands are made of the materials used, which require high degrees of purity. Thus, it is necessary in the case of pharmaceutical active compounds to know the secondary components and to achieve the smallest possible (defined) amounts of impurities, for example metal impurities, in order not to obtain, besides the desired effects, undesired side effects due to the impurities. In the case of organic semiconductors, many properties are specifically dependent on the lowest possible content of trace impurities. Thus, it is entirely possible for properties such as conductivity, charge-carrier mobility or operating lifetime to be changed by several orders of magnitude if impurities in the region of a few ppm are present.

Very few of the materials used are obtained with adequate purity directly from the synthesis. Complex purification procedures are usually necessary in order to achieve the requisite or specified degrees of purity. These consist, for example, of (repeated) recrystallisation, Soxhlet extraction, continuous hot extraction, column filtration and/or chromatography or even zone melting.

It has proven successful to follow the end of the purification procedure by a sublimation or solid distillation and also to repeat this a number of times if necessary in order to remove solvent residues and inorganic impurities, such as salts or metal traces, which are present from catalytic coupling steps or reactor abrasion. Furthermore, a substance separation can also be carried out by fractional sublimation or distillation. This final purification process is of crucial importance for central parameters of the organic electronic device, such as processability, efficiency, voltage and lifetime.

Typically, the material to be purified which is solid at room temperature is converted from the solid or liquid state into the gas phase in a storage vessel (sublimer unit) in vacuo and converted back into the liquid or solid phase in a condensation unit.

In accordance with the prior art, the following sublimation or solid distillation processes are employed for materials in the molecular weight range from about 400 g/mol to 2000 g/mol and sublimation or evaporation temperatures in the range from about 200° C. to 500° C.:

1) Standard Sublimation:
   In sublimation in accordance with the prior art, the sublimation material is heated by a heating source in an evacuated vessel and precipitates on a condenser as sublimate. Conventional designs are described, for example, in Houben-Weyl, 4th Edition, Allgemeine Laborpraxis [General Laboratory Practice], Volumes I/1 and I/2.

2) Carrier-Gas Sublimation:
   In carrier-gas sublimation, a continuous gas stream is passed over the heated sublimation material under reduced pressure. The sublimate precipitates again in a colder zone. Conventional designs are described, for example, in Houben-Weyl, 4th Edition, Allgemeine Laborpraxis [General Laboratory Practice], Volumes I/1 and I/2.

There is still a need for improvement in both processes, as described below:

1) The sublimation in a standard sublimation apparatus begins at the sublimation material/heating surface interface when the sublimation temperature is reached. However, the molecules that have been converted into the gas phase cannot be transported away into the condensation zone at this point, since the sublimation material lying over the sublimation zone blocks the path. Sublimation thus occurs only in the edge region of the sublimation material, which results in the area available for conversion into the gas phase being very small. This results in very low sublimation rates which are unsatisfactory in practice.

2) Although an increase in temperature in order to increase the sublimation rates results in sublimation of the entire surface of the sublimation material, the exceeding of the sublimation temperature that is necessary in order to obtain practicable sublimation rates is frequently so great, owing to the very low thermal conductivity of the materials, that decomposition of the sublimation material occurs. The decomposition typically occurs at the hottest point, the sublimation material/heating surface interface. An ash layer then frequently forms at this point, which acts as insulation layer between the sublimation material/ heating surface interface and thus makes the input of heat into the sublimation material even more difficult.

3) The sublimation in a carrier-gas sublimation apparatus in practice results in similar problems. Here too, poor input of heat and considerable exceeding of the requisite sublimation temperature frequently result in ashing of the materials being observed. In addition, the materials are frequently distributed or entrained over a large region of the apparatus by the carrier-gas stream, which makes removal of the sublimation material a lot more difficult. In addition, the apparatuses are in practice very unwieldy and complex due to the use of long glass tubes having a length of in some cases up to 3 meters, and the apparatuses are very expensive, meaning that economical utilisation of this process is difficult.

Owing to the above-mentioned problems, many of the materials typically used in organic electroluminescent devices, for example organometallic Ir or Pt complexes, such as $Ir(piq)_3$ (tris(phenylisoquinoline)iridium(III)), or styrylamines employed as fluorescent compounds, undergo partial or complete decomposition during sublimation using the standard sublimation processes described above. The same applies to many other materials employed in the area of organic electronics. Only a few very robust materials can be sublimed with a sufficiently high sublimation rate without decomposition using these processes.

A purification process which is related to actual sublimation is solid distillation: some materials which are solid at room temperature melt before practicable sublimation rates or evaporation rates are achieved. After conversion into the melt, these are subjected to solid distillation, where the condensation can take place in the liquid or solid state, depending on the cooling of the condensation unit. The performance of solid distillation in standard sublimation apparatuses in turn has considerable deficiencies. Although, due to convection, the input of heat into the melt is better in this case than in the case of sublimation of a solid, the evaporation surface which corresponds to the melt/gas phase interface is again small here due to the design. In practice, this results in low evaporation rates. In addition, two further problems occur: the melt material always contains small amounts, typically 0.0001% to 1%, of volatile residual solvents from the preceding wet-chemical purification process. These evaporate spontaneously during melting of the organic material and carry droplets of the melt along with them, which contaminate the condensate condensed on the condenser.

A further problem consists in that the condensate, which frequently condenses as organic glass on the condenser, has a very low thermal conductivity which is typical of organic glasses. The heat of condensation consequently can no longer be dissipated adequately even in the case of small condensate layer thicknesses of typically a few millimeters, meaning that the condensate no longer solidifies on the condenser, but instead is produced in liquid form and drips from the condenser back into the melt. This phenomenon limits the amount of substance which can be processed in typical standard sublimation apparatuses to about 50 g, since the temperature stress at evaporation rates in the region of 10 g/h otherwise becomes so great that significant decomposition occurs.

The object of the present invention is therefore to offer technical improvements for this purpose. In particular, a process is desirable in which relatively large amounts of material can be purified or sublimed in a shorter time and with less decomposition. Only the provision of a process of this type makes sublimation on an industrial scale possible in an appropriate manner. The object of the present invention is furthermore to offer a technical improvement for the sublimation of thermally sensitive materials.

Surprisingly, it has been found that sublimation processes can be carried out more efficiently and with considerably less or completely without decomposition if the sublimation material is sublimed under a high vacuum, i.e. a vacuum of usually $<10^{-3}$ mbar, from a rotating vessel, where the sublimation apparatus has a vacuum-tight coupling which is selected from a rotary feedthrough with ferrofluidic seal or a double- or triple-acting mechanical face seal. For some materials, as used, for example, for organic electroluminescent devices, only a process of this type makes sublimation possible at all, whereas these materials decompose completely in standard sublimation processes.

The present invention therefore relates to this process and to an apparatus for carrying out this process.

The prior art discloses sublimation and distillation processes in which the sublimation or distillation material is located in a rotating vessel:

L. C. Craig et al. (*Anal. Chem.* 1950, 22, 1462) describe a distillation process for separating off solvents from dilute solutions. This process consists in setting a flask, which is heated by a water bath and in which the solution is initially introduced, and a collecting flask, into which the solvent is distilled off, in rotation by means of a motor. The apparatus here is connected to a vacuum pump. The coupling of the rotating flask to the vacuum pump by means of the fixed connection takes place via a spherical ground joint which is well greased with joint grease. However, this process is not suitable for work under high-vacuum conditions, since the solvent distilled off partially dissolves the joint grease of the rotating spherical ground joint. The apparatus thus becomes leaky on extended operation, as occurs, in particular, in the case of work on a relatively large scale, which in turn prevents the use of a high vacuum. In addition, the purified product is contaminated by joint grease, which is undesired for the synthesis of high-purity compounds. This process has therefore not become established in industry and has consequently been replaced by other processes.

A further development which may be mentioned is the separating-off of solvents using a rotary evaporator (for example CH 412800). A self-sealing shaft seal, in particular a lip seal, is usually used in rotary evaporators for sealing between rotating and static components. However, these only seal to a vacuum level of about 1 mbar and are thus not suitable for high-vacuum processes.

A further process for the purification of, in particular, relatively small amounts of organic compounds is bulb-tube distillation or sublimation (for example Houben-Weyl, 4th Edition, Allgemeine Laborpraxis [General Laboratory Practice], volumes I/1 and I/2). Here, the compounds are distilled or sublimed in vacuo from a rotating heated flask into a rotating unheated flask, where the seal used between rotating and static components is again usually a lip seal as in the case of the rotary evaporator. These apparatuses are therefore not suitable for large-scale processes under a high vacuum. In the case of very small apparatuses, which are, however, not suitable for purification processes on an industrial scale, a better vacuum than 1 mbar may be possible due to the high suction performance of the vacuum pump with the small apparatus volume and the low leakage rate. However, scale-up of this apparatus for work under a high vacuum is not possible. This apparatus therefore cannot be used for sublimation on an industrial scale.

The invention relates to a process for the purification of chemical substances which are solid at room temperature (the material to be sublimed, called sublimation material below), in which the substance is heated in vacuo, converted into the gas phase and subsequently condensed, where the vessel containing the sublimation material rotates during the operation, characterised in that the process is carried out in an apparatus which has, between the rotating part and the static part, a rotation coupling which is selected from a rotary feedthrough with ferrofluidic seal or a double- or triple-acting mechanical face seal.

A rotation coupling is a coupling of a rotating shaft to a static component.

By means of the process according to the invention, the sublimation material can be converted from the solid state or from the melt into the gas phase. The condensation can likewise take place into the solid phase or into the liquid phase, preferably into the solid phase. A sublimation in the true sense is taken to mean the solid→gaseous→solid transition. A solid distillation in the sense of this invention is taken to mean the solid (at room temperature)→liquid (at elevated temperature)→gaseous→solid or liquid (depending on the cooling temperature) transition. The solid distillation thus takes place from the melt. The process according to the invention relates both to sublimation and also to solid distillation. Both processes alike are called sublimation below in the sense of this invention.

The organic, organometallic or inorganic substances which can be employed for the process according to the invention are initially not restricted, since the process is generally suitable for all compounds which can be evaporated in the given pressure and temperature range. Since the present process achieves particular purification quality, the use is, as described at the outset, suitable for high-value materials, such as, for example, biological or pharmaceutical active compounds or materials for organic electronic applications, especially organic semiconductors.

The chemical substances may be organic, organometallic or inorganic. An organic compound in the sense of this invention is taken to mean a compound which contains at least one carbon atom, preferably a plurality of carbon atoms, and which does not fall under the following definition of an organometallic compound. The organic compound preferably consists predominantly of carbon, hydrogen, deuterium, nitrogen, oxygen, silicon, fluorine, chlorine, bromine, iodine, boron, phosphorus and sulfur. Compounds in which carbon is bonded to non-metals also fall under the definition of organic compounds. An organometallic compound in the sense of this invention is taken to mean a compound in which at least one organic ligand is coordinated to a metal, where the coordination can take place via carbon or another coordinating atom and where "organic ligand" means that the ligand contains at least one carbon atom. An inorganic compound in the sense of this invention is taken to mean either a metal compound which does not fall under the definition given above for an organometallic compound, or an inorganic molecular compound which contains no metals.

Illustrative classes of pharmaceutical active compounds for which the process according to the invention can be used are, in particular, those which have suitable thermal stability. Substances of this type are reviewed, for example, in "Lehrbuch der Pharmakologie und Toxikologie" [Textbook of Pharmacology and Toxicology](E. Mutschler et al., Wissenschaftliche Verlagsgesellschaft, Stuttgart 2003), "Allgemeine und spezielle Pharmakologie und Toxikologie" [General and Specialised Pharmacology and Toxicology](K. Aktories et al.) and in "Deutschen Arzneibuch 2004" [German Pharmacopoeia 2004]. In general, high thermal stability is associated with a relatively high content of aromatic or heteroaromatic structural elements. These are found, for example, in active compounds based on the structural elements benzodiazepine, dibenzoazepine, amphetamine, methadone, heteroaryl- or aryl-substituted acetic and propionic acid preparations, alkaloid preparations, isoquinoline-based substances, stilbene- or diphenylmethane-based substances.

Typical organic semiconductors for which the process according to the invention can be used are generally based on extended cyclic, linear or branched conjugated systems, in particular aromatic or heteroaromatic units, but also linear-conjugated systems, for example stilbene or tolan derivatives. In addition, a multiplicity of organometallic complexes, both of main-group metals (for example Al or Be complexes), and also of transition metals (for example copper, platinum and iridium complexes), also fall into this range. Substances of this type are reviewed, for example, in "Special Issue on Organic Semiconductors and Devices, Part B" (*J. Polym. Sci, Part B: Polym. Phys.* 2003, 41). Typical structure classes are, for example, linear or branched oligoarylenes or -heteroarylenes, spirobifluorene derivatives, indenofluorene derivatives, indenocarbazole derivatives, indolocarbazole derivatives, triarylamine derivatives, extended condensed aromatic compounds (for example anthracene, naphthacene or pentacene derivatives), graphenes, substituted stilbene derivatives and oligostilbene derivatives (for example bis(diarylamino)bisstyrylarylenes), hydroxyquinolinebased aluminium, zinc, beryllium complexes and ortho-metallated iridium and platinum complexes, as described, for example, in WO 05/033244, WO 04/081017 or WO 06/061182. The process according to the invention can furthermore also be employed for precursors which are subsequently converted further into the organic semiconductor, for example for the sublimation of monomers which are subsequently converted into semiconducting polymers.

In general, the process according to the invention can be used for all sublimable compounds in accordance with the prior art. A compound is sublimable in the sense of the present invention if it can be evaporated in the temperature range used and in the pressure range used without or without significant decomposition. Preferred temperature and pressure ranges are described in greater detail below. Sublimation without significant decomposition in the sense of the present invention means that at least 90%, preferably at least 99%, of the compound can be sublimed without decomposition.

The process according to the invention is particularly suitable for the purification of organic and organometallic compounds which have a molecular weight in the range from 300 to 5000 g/mol, preferably from 400 to 2500 g/mol, particularly preferably in the range from 450 to 1500 g/mol. These are preferably defined organic or organometallic compounds.

In the process according to the invention, the sublimation material is heated in the sublimer unit (2) in vacuo in the oven (1) and converted into the gas phase, with the sublimer unit rotating during the sublimation operation. The rotational speed here is preferably in the range from 0.5 to 100 $min^{-1}$, particularly preferably in the range from 1 to 20 $min^{-1}$, very particularly preferably in the range from 1.5 to 10 $min^{-1}$, in particular in the range from 2 to 5 $min^{-1}$. The rotation here is usually only switched on after the heating, but may also be switched on before the heating. The temperature here is adjusted via the sublimation or evaporation temperature given at the respective pressure until a technically useful evaporation rate is achieved. In general, it is preferred for the evaporation rate to be as high as possible. A technically useful evaporation rate is in the range between 10 and 1000 g/h, depending on the application and depending on the class of active compound. Depending on the class of compound, even an evaporation rate in the range between 1 and 10 g/h may also be technically useful. This is useful, in particular, in the case of organometallic compounds, as are employed for organic semiconductor components, since it is frequently difficult to sublime these compounds at all without decomposition. The evaporation here, as described above, can take place both from the solid and also from the melt.

The sublimation or evaporation temperature of the compounds here at a pressure in the range from $10^{-3}$ to $10^{-6}$ mbar is frequently higher than 200° C. and frequently even higher than 250° C. This applies, in particular, to organic semiconductors, as are usually employed in electronic devices.

The sublimation material is preferably converted into the gas phase at a temperature in the range from 200° C. to 500° C., particularly preferably in the range from 250° C. to 450° C., very particularly preferably in the range from 250° C. to 400° C. The sublimation temperature here depends on the material, where the lowest possible sublimation temperature and therefore the best possible vacuum is preferred in order to prevent thermal decomposition.

The vacuum used is usually in the range from less than $10^{-3}$ to $10^{-8}$ mbar, preferably in the range from less than $10^{-3}$ to $10^{-7}$ mbar, particularly preferably in the range from $10^{-4}$ to $10^{-6}$ mbar. These values apply, in particular, to processes which are carried out without injection of carrier gas. The pressure ranges used are preferably achieved by a multistage vacuum-pump system.

In an embodiment of the invention, the process is carried out as fractional sublimation, i.e. a plurality of fractions of the sublimed material are collected. A fractional sublimation of this type can also be used for the separation of mixtures, for example for the separation of stereoisomer mixtures.

The process according to the invention is preferably carried out under dynamic vacuum. The apparatus is thus constantly connected to the vacuum-pump system while the process is carried out. This has the advantage over static vacuum that a better vacuum can thereby be achieved.

In a further embodiment of the process according to the invention, the process is carried out using an inert carrier gas. If a carrier gas is used, the process according to the invention is preferably carried out in a pressure range from $10^{-1}$ to $10^{-4}$ mbar. This enables the conversion into the gas phase to be accelerated. In this way, it is possible to lower the effective evaporation/sublimation temperature in the case of sensitive substances in order to prevent decomposition. Alternatively, a higher sublimation rate can be achieved at the same temperature. The carrier gas used can generally be inert gases, for example nitrogen, helium, argon, krypton, xenon or sulfur hexafluoride. If the apparatus has a cold trap, use should be made of a carrier gas which does not condense in the cold trap and thus block the cold trap. If the cold trap is operated at the temperature of liquid nitrogen (−196° C.), a suitable carrier gas is, in particular, helium.

In a further embodiment of the invention, the process is carried out semi-continuously. To this end, fresh sublimation material is preferably fed into the sublimer unit in the melt. This has the advantage that only little sublimation material is always present in the sublimer unit, which thus means only low temperature stress for the material.

The process according to the invention is preferably carried out as follows: the sublimation material, which should already be well dried, is initially introduced into the sublimer unit. The apparatus is closed, and a vacuum is applied. In an embodiment of the invention, the heating is initially carried out without rotation, and the rotation is only switched on when or just before the actual sublimation temperature is reached. This enables dusting of the material to be sublimed to be prevented or at least reduced. This applies, in particular, if the material is evaporated from the melt. It is preferred here during heating for material not to be heated directly to the sublimation temperature, but instead for the temperature to be increased stepwise in order firstly to remove the residual solvent which is usually still present from the product at relatively low temperature. In particular in the case of sublimation on a relatively large scale, it is appropriate firstly to determine the suitable sublimation temperature on a relatively small scale. If the sublimation material has melted or if the sublimation temperature has been reached or virtually reached in the case of sublimation from the solid state, the rotation is switched on. After completion of the sublimation, the sublimed material is removed from the condensation unit(s).

The present invention likewise relates to an apparatus for carrying out the process according to the invention. The apparatus according to the invention is shown diagrammatically in FIG. 1.

Figure 1:
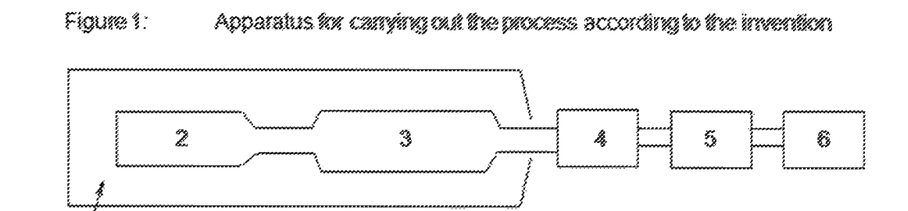
FIG. 1 schematically illustrates an apparatus for carrying out the process according to the invention.

The invention therefore furthermore relates to an apparatus for the sublimation of chemical compounds, comprising an oven (1), a sublimer unit (2), a condensation unit (3), which is in contact with the sublimer unit, a rotation drive (4) for rotation of the sublimer and condensation units, and a vacuum pump or vacuum-pump system (6), characterised in that the apparatus has, between the rotating part and the fixed part, a rotation coupling (5), which is selected from a rotary feedthrough with ferrofluidic seal or a double- or triple-acting mechanical face seal.

The apparatus according to the invention in which the process according to the invention can be carried out is described in detail below:

The oven (1) in FIG. 1 is depicted in such a way that it surrounds both the sublimer unit (2) and the condensation unit (3). For this purpose, it is necessary for the oven to have various temperature zones, where the temperature of the sublimer unit is higher than that of the condensation unit. In an alternative embodiment of the present invention, the oven (1) may also only surround the sublimer unit (2), while the condensation unit (3) is arranged outside the oven.

In general, all heating methods as are used in accordance with the prior art are suitable for the oven (1). The heating can take place either indirectly (vessel wall/jacket is heated, for example by hot air, heating bath, heating mantle, radiant heat, etc.) or directly (for example via IR or microwave coupling-in). It is also possible to mix the sublimation material with metal particles (beads) and to heat these metal particles inductively. In a preferred embodiment, the heating takes place by indirect heating, preferably by hot gas, so that the oven is preferably a hot-air oven. This method offers the advantage that a hot-air oven can be heated rapidly due to its low heat capacity and can be cooled again rapidly after completion of the purification operation. Furthermore, this method offers greater safety due to the absence of ignition sources. An active cooling operation by the introduction of air at room temperature is also possible in this way. It is preferred for an oven to be selected with which the desired temperature can be set selectively and regulated in a controlled manner. The thermal stress of the materials, some of which are heat-sensitive, and decomposition of the materials are thereby reduced. It is preferred for the temperature to be determined at various points in the oven in order to be able to control the process accurately.

In a further preferred embodiment of the invention, the oven (1) can be divided into various heating zones, in each of which the temperature can be set selectively, i.e. the oven is preferably constructed in such a way that zone-wise temperature setting is possible. This is possible, in particular, in the case of radiation ovens and hot-air ovens. Thus, for example, a plurality of radiation sources or hot-air sources can be used, and the individual heating zones in the oven can be insulated or at least screened off thermally from one another. This is depicted diagrammatically in FIG. 4, where (1) to (6) have the same meaning as described for FIG. 1. (1a) to (1d) stand for separate heating sources, where the following applies to the temperatures: $T_{(1a)} > T_{(1b)} > T_{(1c)} > T_{(1d)}$. (1e) represents the thermal screening-off of the heating zones from one another.

Figure 4:
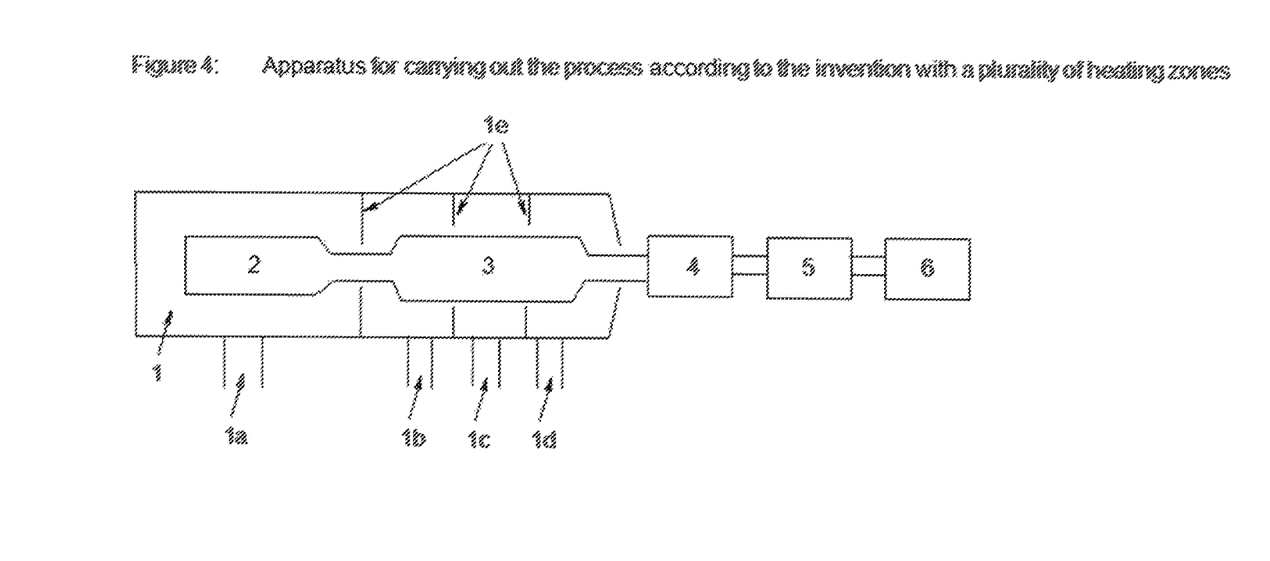
FIG. 4 illustrates an apparatus for carrying out the process according to the invention with a plurality of heating zones.

This may have advantages since it also enables the condensation unit to be introduced into the oven, enabling fractional sublimation and thus still further purification of the material due to the various temperature zones of the oven.

In a preferred embodiment of the invention, the hot air in the case of the use of a hot-air source is not passed directly to the sublimer unit in order to prevent overheating of the vessel wall and the associated risk of thermal decomposition of the sublimation material. Instead, the hot air is preferably deflected between the hot-air source and the sublimer unit, for example by a static plate (deflector plate, baffle plate) or metal fabric introduced in between, by rotating fan blades or another suitable deflection device. This enables uniform heating of the entire sublimer unit to be achieved.

The sublimer unit (2) is the unit into which the sublimation material is introduced and from which the sublimation material is evaporated, while the condensation unit (3) is the unit on which the sublimed material is condensed. The condensation unit here may consist of one or more vessels.

The sublimer unit (2) and the condensation unit (3) are described in greater detail below.

In an embodiment of the invention, the sublimer unit (2) is connected to the condensation unit (3) in a vacuum-tight manner, for example by a flange, and the vacuum is applied directly to the sublimer and condensation units. This corresponds to the diagrammatic representation in FIG. 1.

Figure 5:
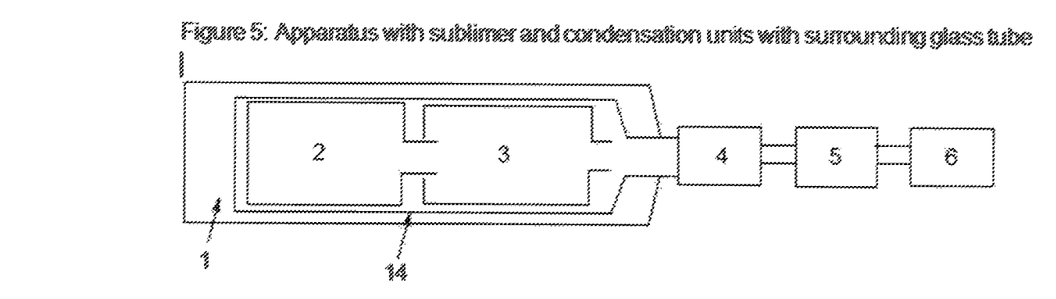
FIG. 5 illustrates an apparatus with sublimer and condensation units with surrounding glass tube.

In a further embodiment of the invention, the sublimer unit (2) and the condensation unit (3) are surrounded by a tube, for example a glass tube, and the vacuum is applied to the surrounding glass tube. This tube is connected to the remainder of the apparatus, for example by means of a ground-glass joint or a flat glass flange. The sublimer unit and the condensation unit are inserted into the surrounding tube. This embodiment has proven advantageous since loading of the apparatus with the sublimation material and removal of the sublimed material are thereby simpler. For this embodiment, it is furthermore sufficient for the surrounding tube to have adequate vacuum stability, while the sublimer and condensation units do not have to meet this requirement. This embodiment is depicted diagrammatically in FIG. 5, where units (1) to (6) have the same meaning as described for FIG. 1, and (14) stands for the tube which surrounds the sublimer and condensation units. In this embodiment of the invention, the sublimer unit (2) and the condensation unit (3) are usually not connected to one another in a vacuum-tight manner, but instead are only placed loosely against one another or pushed into one another.

The sublimer unit (2) is initially not restricted. Thus, for example, glass vessels, ceramic vessels, vessels made from corundum, boron nitride or graphite or also vessels made from various steel or metal variants are suitable. Graphite has the advantage that it can also be heated inductively. In a preferred embodiment of the invention, glass vessels are used. Preference is given to the use of quartz or Duran glass (borosilicate 3.3).

Figure 6:
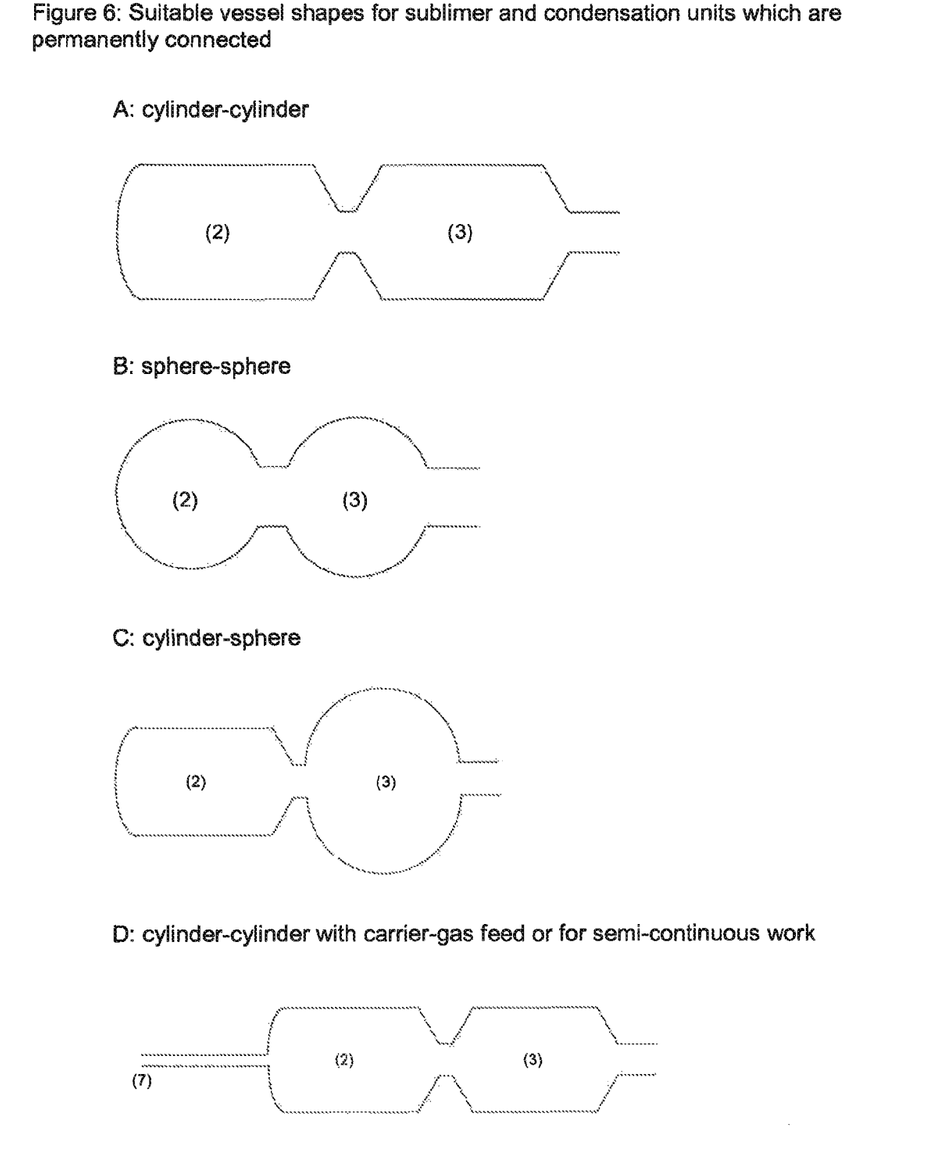
FIG. 6 illustrates suitable vessel shapes for sublimer and condensation units which are permanently connected.
Figure 7:
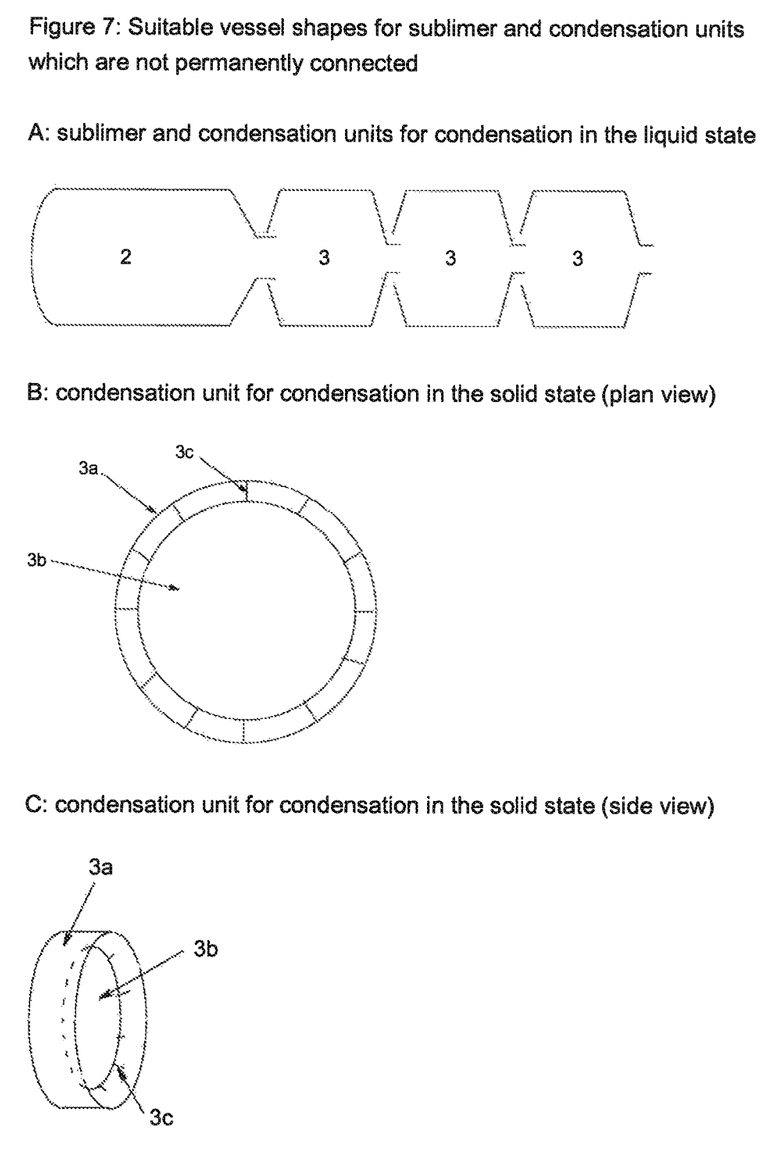
FIG. 7 illustrates suitable vessel shapes for sublimer and condensation units which are not permanently connected.

The vessel geometry may vary (FIGS. 6 and 7). Thus, spheres, cylindrical vessels, but also tubes and further curved shapes are possible. In a preferred embodiment of the invention, the sublimer unit used is a cylindrical vessel having a rounded-off or outwardly curved base. This vessel shape has proven particularly suitable, since it has a larger surface area in relation to the volume than a round flask.

In an embodiment of the invention, the apparatus with the sublimer unit and the condensation unit is arranged horizontally. In a further embodiment of the invention, the entire apparatus and thus also the sublimer unit and condensation unit are tilted to the horizontal, where angles of 1 to 10° are preferred, and the sublimer unit is arranged lower than the condensation unit. An apparatus tilt of this type has the advantage that the sublimer unit can accommodate relatively large amounts of material, and the same apparatus is thus suitable for the sublimation of relatively large amounts. A disadvantage does not arise through the tilt of the apparatus, since the sublimed material is usually formed either in solid form as glass or condenses in liquid form in the condensation unit and thus has a higher density than the material to be sublimed, which is usually introduced into the sublimer unit in powder form.

In addition to the sublimation material, grinding bodies may also be added to the sublimer unit (2). These result in better mixing of the material and thus in more uniform temperature distribution and better sublimation rates. Furthermore, they result in comminution of the sublimation material, for example through grinding of crystals. A relatively large surface area of the sublimation material thus arises, which in turn results in faster sublimation. The grinding bodies used are preferably beads or approximately spherical bodies. These preferably have a diameter of 1 to 10 mm, particularly preferably 2 to 6 mm, where bead mixtures of various diameter have proven particularly suitable. Preferred materials for the grinding bodies are selected from glass or metal, particularly preferably from quartz or Duran glass. The grinding bodies are particularly preferably selected from the same material as the sublimation apparatus.

Figure 3:
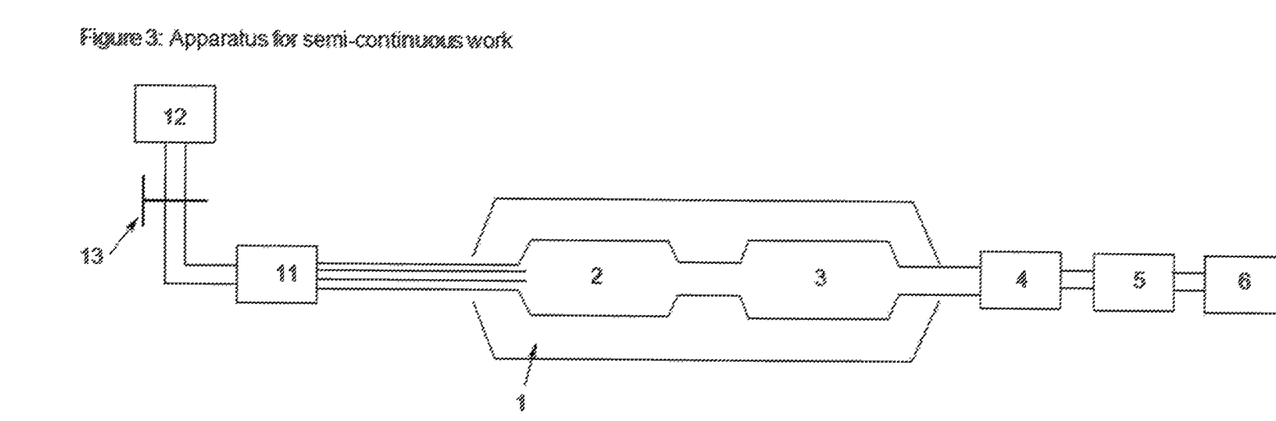
FIG. 3 illustrates an apparatus for semi-continuous work.

The evaporated material is condensed on the condensation unit (3) in a less-hot zone within the oven or even outside the oven. The condensation unit usually rotates at the same speed as the sublimer unit. The condensation unit (3) may be permanently connected to the sublimer unit (2) (FIG. 6). The sublimer unit (2) and the condensation unit (3) may also be connected to one another, for example, by a flange, where, due to the high temperature requirement, this is sealed by means of a heat-stable seal, for example a Kalrez seal, a gold seal or a graphite seal. The connection between the sublimer unit (2) and the condensation unit (3) is preferably heated in order that material cannot sublime in this region and thus block the relatively narrow connection between the two vessels. In a preferred embodiment of the invention, however, the condensation unit is, as described above, not permanently connected to the sublimer unit (FIG. 7). This simplifies removal of the sublimed product and cleaning of the sublimer and condensation units. As described above, it is preferred for the sublimer and condensation units to be inserted into a tube, to which the vacuum is then applied.

The condensation unit (3) may consist of various materials, for example glass, metal or ceramic, but also of surfaces having low surface energies, in particular having surface energies of less than 70 mN/m, for example PTFE, as described, for example, in DE 102005038211, where the same definition of surface energy as described therein applies. A condensation unit made from glass, metal or ceramic which is coated with a material having low surface energy, for example PTFE, is likewise suitable. In a preferred embodiment of the invention, the condensation unit consists of glass. This has the advantage that the transparency of the apparatus enables the sublimation and condensation process to be followed. It is also possible to construct the condensation unit from more than one corresponding material. This may take place in the sense of a composite material, but also in the sense of a coating.

Various vessel geometries are suitable for the condensation unit (3), for example the same ones as described above for the sublimer unit, such as cylindrical or spherical units. The preferred geometry of the condensation unit also depends on whether the sublimed material condenses in the solid or liquid state.

If the sublimed material condenses in the liquid state, the condensation unit is preferably cylindrical or spherical, in particular cylindrical, where it has a narrowing and an opening at both ends, at which it is connected loosely or by means of a seal to the sublimer unit on the one hand and optionally to the next condensation unit, if a plurality of condensation units are present, on the other hand, or to two condensation units if a plurality of condensation units are present. This is depicted diagrammatically in FIG. 6A. On further cooling, the material condensed in the liquid state solidifies, where the solid material is frequently obtained in the form of a glass. On solidification, the glass-like material frequently also detaches directly from the condensation unit and can thus be removed easily after completion of the sublimation. If the sublimed material does not detach of its own accord, it is detached mechanically from the condensation unit, for example by scraping, after completion of the sublimation.

If the sublimed material condenses directly in the solid state, the condensation unit described above can likewise be used. Furthermore, cylindrical units which have a disc inside the cylinder ring on which the condensation of the sublimed material can take place have proven suitable for the condensation unit in the case of condensation in the solid state. This is depicted diagrammatically in FIG. 6B in plan view and in FIG. 6C in side view, in each case for a condensation unit. (3a) here stands for the outer cylinder ring, (3b) stands for the disc on which the condensation takes place and (3c) stands for the connections which stabilise the disc inside the cylinder ring. For fractional sublimation, a plurality of these units can be placed against one another, so that a plurality of such condensation units are present which can be heated to different temperatures. The removal of the sublimed material after completion of the sublimation is usually carried out mechanically, for example by scraping.

The condensation unit (3) here is operated at a temperature which is sufficiently far below the sublimation or evaporation temperature (at a given pressure) in order to facilitate adequate condensation. The condensation here can take place into the liquid state or into the solid state. In the case of relatively small sublimation devices and in the case of low sublimation rates, even air cooling or cooling by a gas stream, for example an air or nitrogen stream, may be sufficient here. However, it may also be advantageous to bring all or part of the condensation unit to a (constantly) low temperature, for example by water cooling. Spherical condensation units in particular have the advantage that they can easily be cooled by dipping into a cooling bath, for example a water or ice bath. The entire unit is cooled uniformly by the rotation of the unit. The cooling temperature is preferably selected so that the sublimate is obtained in the glass-like state. This is achieved by cooling to below the glass-transition temperature. The sublimate can thus be removed from the apparatus more easily. In general, however, active cooling of the condensation unit is not necessary.

Depending on the product specification, it may be appropriate or necessary, as already described above, instead of only one condensation unit, to use a plurality of condensation units, for example a plurality of flasks or cylinders arranged one behind the other or a plurality of the condensation units described in greater detail above which are heated to different temperatures in order in this way also to effect further purification through the separation of co-evaporated impurities. In this way, the separation of product mixtures which can otherwise only be separated with difficulty can likewise be facilitated, for example the separation of stereoisomers of a product. Thus, for example, the separation of diastereomers, for example atropisomers of a compound, by this process is facilitated, while the separation by processes in accordance with the prior art, for example by sublimation in accordance with the prior art, does not give satisfactory results here.

The rotation coupling (5) is in accordance with the invention a rotary feedthrough with ferrofluidic seal or a double- or triple-acting mechanical face seal.

The rotation of the evaporator/sublimer unit can take place, for example, in such a way that the evaporator/sublimer unit is mounted on a hollow shaft made from metal or glass. This hollow shaft is driven by a variable motor via a toothed belt. In each case here, it should be possible both to regulate and control the rotational speed.

FIG. 1 furthermore shows the rotation drive (4) and the rotation coupling (5) as separate elements. In an alternative embodiment of the invention, the rotation drive may also be integrated into the rotation coupling, so that this is a single element. In particular for the rotary feedthrough with ferrofluidic seal, such a combination of rotation drive and rotation coupling is commercially available.

Since the process according to the invention is preferably carried out in a pressure range up to $10^{-7}$ mbar, corresponding demands are made of the rotation coupling. In accordance with the invention, a double- or triple-acting mechanical face seal (for example U.S. Pat. No. 6,976,681) or a rotary feedthrough with ferrofluidic seal is used. These rotation couplings are generally already known in the prior art and are commercially available. Since heat is generated by the rotation of the coupling, it may be preferred to cool the coupling, in particular in the case of relatively large sublimation apparatuses. The cooling can be carried out, for example, by a gas stream or by water.

The requisite pressure ranges are preferably achieved by a multistage vacuum-pump system (6), preferably by a two-stage vacuum-pump system. A pre-pump having a suction performance of 5-50 $m^3/h$, for example an oil pump, a dry-running scroll pump, a rotary vane pump or a Roots pump, generates a pre-vacuum in the range from about $5\times10^{-2}$ to $5\times10^{-1}$ mbar. Connected thereto is a high-vacuum pump, for example a turbomolecular pump or an oil diffusion pump, with which a vacuum in the desired range can be achieved in each case. It may be appropriate to install a cold trap or a baffle, in which solvent residues present in the sublimation material and further volatile by-products are condensed, between the vacuum pump and the actual sublimation apparatus. This enables the pressure to be reduced further again. The cold trap or the baffle furthermore serves to protect the vacuum pump and prevent back-diffusion of pump constituents, such as, for example, oil, into the apparatus. The combination of a scroll pump with a turbomolecular pump offers the advantage that an absolutely oil-free vacuum can be generated thereby. This combination is therefore preferred. Furthermore, the apparatus can have a manometer for pressure measurement of the apparatus. This may also be appropriate in order to follow and control the sublimation process, since the beginning of the sublimation is indicated by a slight pressure increase and the end of the sublimation is indicated by a further pressure drop.

The apparatus may also have further elements which are not absolutely necessary, but whose presence may be appropriate. Thus, for example, the presence of a thermometer and/or a manometer is appropriate for monitoring of the sublimation process. For large and thus heavy apparatuses, it may also be appropriate or necessary for the sublimer unit to be supported by a rotating bearing at its closed end. The use of a process control system may also be appropriate.

Figure 2:
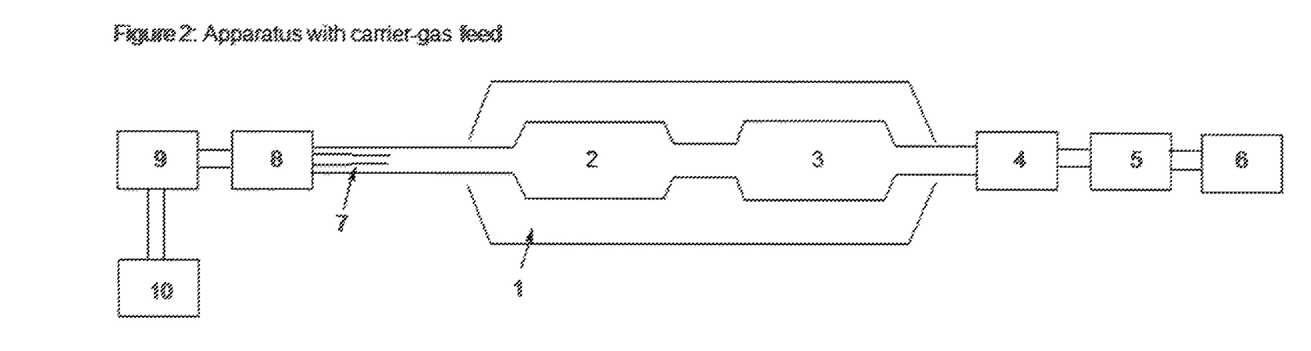
FIG. 2 illustrates an apparatus with carrier-gas feed.

An apparatus for carrying out a carrier-gas sublimation requires further elements, for example an inert-gas feed, as shown in FIG. 2. Constituents (1) to (6) of the apparatus in FIG. 2 have the same meaning as described for the apparatus in FIG. 1. This apparatus furthermore has the following elements:
(7) gas feed tube;
(8) rotation coupling;
(9) metering valve;
(10) gas source.

The carrier gas is preferably fed coaxially into the sublimer unit. To this end, the evaporator unit is provided with a carrier-gas feed tube (7), which leaves the oven in coaxial form. It may be preferred to preheat the carrier gas before feeding into the sublimer unit. The coupling to the static metering valve (9), which is connected to the gas source (10), for example a gas bottle, can be carried out by means of a further rotation coupling (8). This is likewise preferably a rotary feedthrough with ferrofluidic seal or a double- or triple-acting mechanical face seal.

An apparatus for semi-continuous work is shown in FIG. 3. Constituents (1) to (6) of the apparatus in FIG. 3 have the same meaning as described for the apparatus in FIG. 1. This apparatus furthermore has the following elements:
(11) rotation coupling;
(12) storage vessel;
(13) metering device.

The rotation coupling (11) here is likewise preferably a rotary feedthrough with ferrofluidic seal or a double- or triple-acting mechanical face seal.

As for the carrier-gas supply, the apparatus for semi-continuous work also has a feed tube at one end of the sublimer unit. The feed into the sublimer unit here is in principle possible from both sides of the sublimer unit. This is connected via a further rotating seal (11) to the storage vessel (12), which contains the optionally heated material in the liquid or solid state. This can be metered into the sublimer unit via a stop cock or another metering device (13). It may be appropriate for the feed tube to be heated in order to facilitate the feed of the melt without solidification.

Since high-purity materials are purified by the process according to the invention or using the apparatus according to the invention, the greatest possible cleanliness of the apparatus itself must be ensured. Thus, it is preferred for both the sublimer unit and also the condensation unit to be cleaned very well before carrying out a sublimation. For this purpose, cleaning of the corresponding sublimer unit and condensation unit by calcination or firing may also be preferred, causing impurities to be thermally decomposed.

The process according to the invention and the apparatus according to the invention have the following surprising advantages over the prior art:

1. The process according to the invention enables significantly larger amounts of material to be sublimed per batch than is possible in accordance with the prior art.
2, The thermal load of the material to be sublimed is considerably lower than in the case of devices in accordance with the prior art. This enables losses of the material to be avoided. For some thermally sensitive materials which decompose completely on sublimation in accordance with the prior art, only the process according to the invention makes sublimation possible at all. Furthermore, the uniform input of heat means that no or at least significantly less ashing of the material is observed.
3. Due to the good mixing, the sublimation proceeds considerably more quickly than with apparatuses in accordance with the prior art, which represents a significant technical advantage.
4. The process according to the invention also offers considerable advantages for sublimation in which the evaporation takes place from the melt. Thus, apart from the advantages mentioned above, it should be emphasised that residual solvents in the melt are unproblematic here, since, due to the rotation, uniform evaporation is achieved and boiling delays due to evaporating solvent are avoided. Contamination of the sublimed material is thus avoided. Furthermore, it is unproblematic with the process according to the invention if the compound condenses in the liquid state and not in the solid state, since reflux of the purified material into the as yet unpurified material cannot occur here.
5. The process according to the invention can also be carried out using carrier gas, resulting in a further acceleration of the sublimation process and in addition a reduction in the sublimation temperature. This process is therefore particularly suitable for thermally sensitive substances.
6. The process according to the invention can also be carried out semi-continuously, enabling sublimation on a still larger scale with simultaneous reduction of the thermal stress for the material to be sublimed.

The present invention is explained in greater detail by the following examples, without wishing to restrict it thereto. The person skilled in the art will be able to find further embodiments from the description and the examples indicated without inventive step or naturally purify further materials using the process described. In particular, scaling of the apparatus and work on a larger scale are also possible without inventive step.

Description of the Figures

The numbers indicated in the figures are explained in detail in the description above and in the working examples.

FIG. 1: Apparatus for carrying out the process according to the invention

FIG. 2: Apparatus with carrier-gas feed

FIG. 3: Apparatus for semi-continuous work

FIG. 4: Apparatus for carrying out the process according to the invention with a plurality of heating zones FIG. 5: Apparatus with sublimer and condensation units with surrounding glass tube FIG. 6: Suitable vessel shapes for permanently connected sublimer and condensation units: A) cylinder-cylinder; B)

sphere-sphere; C) cylinder-sphere; D) cylinder-cylinder with carrier-gas feed or for semi-continuous work FIG. 7: Suitable vessel shapes for sublimer and condensation units which are not permanently connected: A) sublimer and condensation units for condensation in the liquid state; B) condensation unit for condensation in the solid state (plan view); C) condensation unit for condensation in the solid state (side view)

Figure 8:
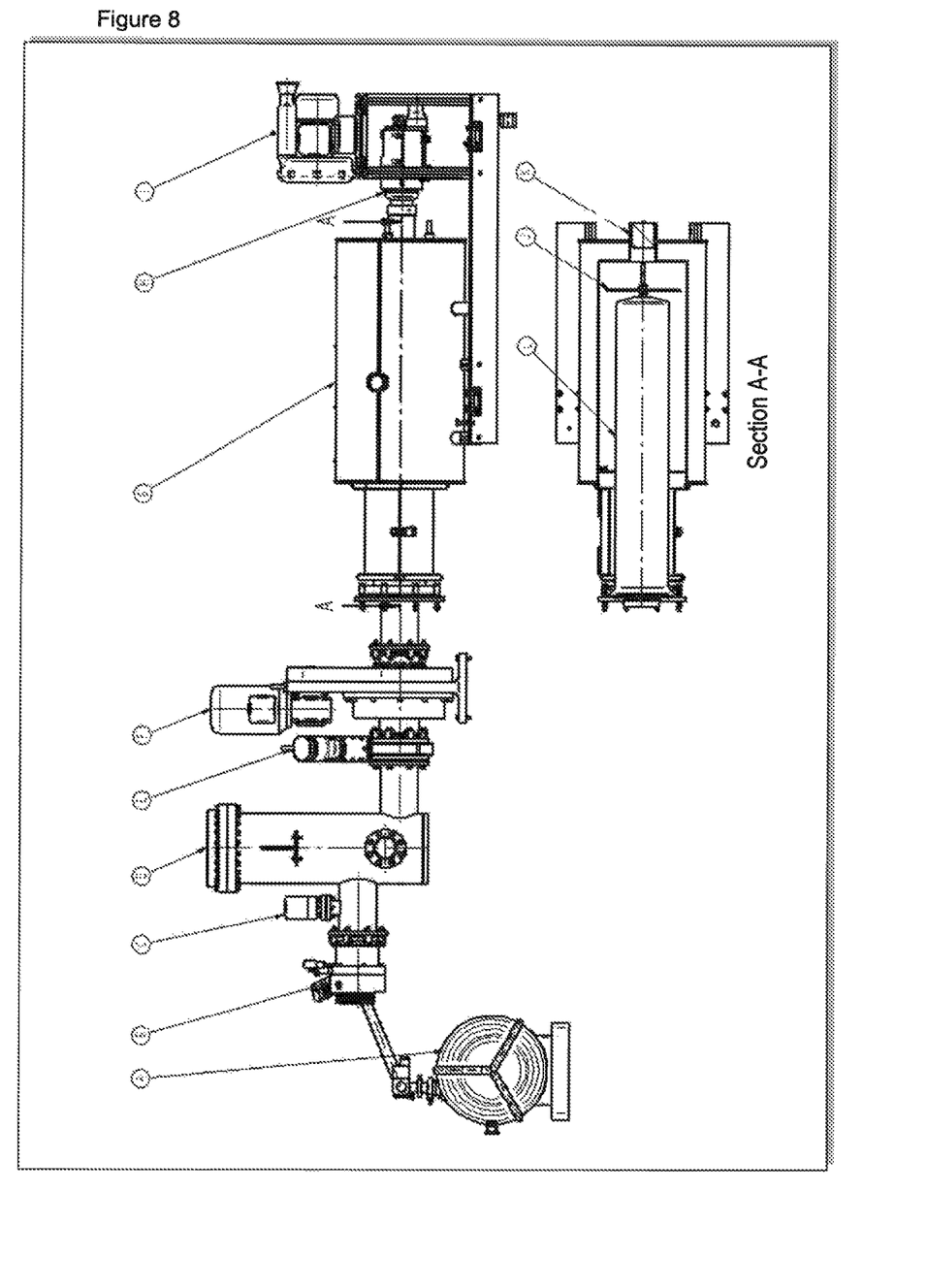
FIG. 8 illustrates a complete design of the sublimation apparatus according to the invention.

FIG. 8: Overall view of the sublimation apparatus according to the invention, design drawing

EXAMPLES

Example 1: Structure of an Apparatus in Accordance with the Prior Art for Carrying Out the Sublimation (Comparison), Apparatus 1

Components:
 4 l single-necked glass flask made from Duran glass from Schott Mainz, provided with an NS 45 conical ground-glass joint socket,
 glass tube with a length of 1 m (internal diameter 40 mm), provided at one end with an NS 45 conical ground glass joint cone, provided at the other end with a flat flange,
 controllable heating hood,
 turbo drag pump stand,
 cold trap, can be filled with liquid nitrogen.

A certain amount of compounds MAT1 to MAT6 to be sublimed is initially introduced in the 4 l single-necked glass flask (see Example 4, Table 2). The single-necked flask is provided with the glass tube, the NS 45 conical ground glass joint cone is sealed with Teflon rings. This unit is connected to the turbo drag pump stand via the flat flange and positioned in the controllable heating hood. The apparatus is evacuated until a vacuum has been achieved in the rest state (see Example 4, Table 2). The temperature is subsequently increased stepwise in 20° C. steps to the sublimation temperature indicated in Table 3 by means of the heating hood. When the sublimation is complete, the apparatus is allowed to cool to room temperature, the vacuum is released, the sublimate which has accumulated on the upper half of the flask is removed mechanically and sent for purity analysis by NMR or HPLC.

Example 2: Structure of an Apparatus According to the Invention for Carrying Out the Sublimation, Apparatus 2

The sublimation apparatus according to the invention comprises the components depicted diagrammatically in FIG. 1. The complete design drawing is depicted in FIG. 8. The individual components have the following meanings here:
A) pre-pump for generating a pre-vacuum
B) turbomolecular pump for generating a high vacuum
C) manometer for vacuum measurement
D) cold trap, cooled using liquid nitrogen
E) spool valve, for separation of sublimation space and pump stand
F) rotary feedthrough with ferrofluidic seal and electric drive
G) hot-air oven consisting of an insulated V2A tube (diameter 250 mm, length 450 mm), provided with four PT100 thermoelements for temperature control
H) air heater for oven heating
I) fan for air heater
J) baffle for flow management in the oven
K) air inlet into oven
L) sublimation vessel consisting of sublimer unit and condensation unit A certain amount of compounds MAT1 to MAT6 to be sublimed is initially introduced in the sublimer unit (2) or (L) (see Example 4, Table 2). The sublimer unit according to the invention is assembled and evacuated to the base pressure (see Example 4, Table 2). The rotation is subsequently switched on (rotational speed 1.5 min$^{-1}$), and the temperature is increased stepwise in 50° C. steps to the sublimation temperature indicated in Table 2 by means of the hot-air oven. When the sublimation is complete, the apparatus is allowed to cool to room temperature, the vacuum is released, the sublimate which has accumulated in the condensation unit is removed mechanically and sent for purity analysis by NMR or HPLC.

Example 3: Structure of an Apparatus According to the Invention for Carrying Out the Carrier-Gas Sublimation, Apparatus 3

The sublimation apparatus according to the invention consists of the components depicted in FIG. 2, which are arranged one after the other and are connected by commercially available corrugated vacuum hoses with O-ring flanges, analogously to FIG. 8.

A certain amount of compounds MAT4 and MAT6 to be sublimed is initially introduced in the sublimer unit (2) (see Example 4, Table 2). The sublimer unit according to the invention is assembled and evacuated to the base pressure (see Example 4, Table 2), and the rotation is switched on (rotational speed 1 min$^{-1}$). The temperature is subsequently increased stepwise in 50° C. steps to the sublimation temperature indicated in Table 2 by means of the hot-air oven. When the sublimation temperature has been reached, the helium carrier-gas stream is adjusted so that the pressure indicated (see Example 4, Table 2) is achieved. When the sublimation is complete, the apparatus is allowed to cool to room temperature, the vacuum is released, the sublimate which has accumulated in the condensation unit is removed mechanically and sent for purity analysis by NMR or HPLC.

Example 4: Sublimations of Various Organic and Organometallic Substances

The following organic substances MAT1 to MAT6 (overview Table 1) are evaporated in the above-mentioned apparatuses and thus purified:

TABLE 1

Material overview

| | Chemical name | Literature | Melting point [° C.] | Molecular weight [g/mol] | Purity (acc. to HPLC) |
|---|---|---|---|---|---|
| MAT1 | 9,10-Bis-(2-spirobi-fluorenyl)anthracene | WO 04/58911 | 463 | 807.0 | 99.7% |

TABLE 1-continued

Material overview

| | Chemical name | Literature | Melting point [°C.] | Molecular weight [g/mol] | Purity (acc. to HPLC) |
|---|---|---|---|---|---|
| MAT2 | Bis-(2-spirobifluorenyl) ketone | WO 04/93207 | 384 | 658.8 | 99.98% |
| MAT3 | 2,2',7,7'-Tetrakis-(bis-p-tolylamino)spirobifluorene | JP 03/124472 | 296 | 1097.5 | 99.95% |
| MAT4 | Tris(4-(trimethylsilyl-phenylvinyl)phenyl)amine | DE 102005058543.4 | — | 768.3 | 99.5% |
| MAT5 | fac-Tris[2-(2-pyridinyl-κN)phenyl-κC]-iridium(III) | WO 02/060910 | Decomp. | 768.3 | 99.95% |
| MAT6 | fac-Tris[7,7-dimethyl-8-fluoro-4-methyldibenzo-[de,h]quinoline-$C^2$,N]-iridium(III) | WO 05/033244 | Decomp. | 901.0 | 99.9% |

An overview of the sublimation experiments carried out is reproduced in Table 2.

TABLE 2

Sublimation overview

| No. | Material | Amount used [g] | Sublimer | Sublimation conditions ($T_{oven}$; p; phase; addition) | Observations |
|---|---|---|---|---|---|
| 1 | MAT1 | 200 | App. 1 (comparison) | 450° C.; 4 × $10^{-5}$ mbar; from the solid phase | Sublimation time: 8 h, purity of sublimate: 99.4%, decomposition products: 0.3%. An ash layer forms over time at the glass flask/sublimation material interface. Crystals measuring up to several mm form on the surface of the sublimation material. Towards the end of the sublimation, ash is entrained, contaminating the sublimate. |
| 2 | MAT1 | 200 | App. 2 | 400° C.; 3 × $10^{-5}$ mbar; from the solid phase, addition of 150 g of glass beads (diameter 5 mm) | Sublimation time: 1 h 40 min, purity of sublimate: 99.7%, decomposition products: none. Neither ash nor large crystals form. The sublimation proceeds completely and without problems. |
| 3 | MAT2 | 100 | App. 1 (comparison) | 390° C.; 5 × $10^{-5}$ mbar; from the solid phase | Sublimation time: 2 h 30 min, purity of sublimate: 99.98%, decomposition products: none. Small amounts of an ash/salts from the synthesis are entrained towards the end of the sublimation. |
| 4 | MAT2 | 300 | App. 1 (comparison) | 390° C.; 5 × $10^{-5}$ mbar; from the solid phase | Sublimation time: 7 h 30 min, purity of sublimate: 99.98%, decomposition products: none. The sublimate preferentially deposits at the transition from the heated to the unheated zone. The interior of the flask slowly becomes blocked from the edge. After 5 h, there is a danger of blockage over the entire flask cross section. The sublimation has to be terminated. |

TABLE 2-continued

Sublimation overview

| No. | Material | Amount used [g] | Sublimer | Sublimation conditions ($T_{oven}$; p; phase; addition) | Observations |
|---|---|---|---|---|---|
| 5 | MAT2 | 1000 | App. 2 | 375° C.; $3 \times 10^{-5}$ mbar; from the solid phase; addition of 500 g of glass beads (diameter 5 mm) | Sublimation time: 6 h 30 min, purity of sublimate: 99.98%, decomposition products: none. The sublimation proceeds completely and without problems. Little ash/salts from the synthesis remain in the sublimer unit. These are not entrained into the sublimate. |
| 6 | MAT3 | 50 | App. 1 (comparison) | 390° C.; $3 \times 10^{-5}$ mbar; from liquid phase | Sublimation time: 7 h, purity of sublimate: 99.75%, decomposition products: 0.2%. After melting at 305° C., solvent residues from the recrystallisation are liberated, These result in boiling delays and splashing. The condensation surface is contaminated by splashes. After sublimation of about 30 g, the transport of heat away at the condensation surface is so poor that the condensate no longer solidifies and runs back on the flask wall. |
| 7 | MAT3 | 500 | App. 2 | 380° C.; $4 \times 10^{-5}$ mbar; from liquid phase | Sublimation time: 3 h, purity of sublimate: 99.95%, decomposition products: none. At 305° C., the material melts. The pressure increases due to liberated residual solvent for 20 min. to $1 \times 10^{-2}$ mbar. However, no boiling delays and thus no splashing occur. The actual sublimation at 380° C. proceeds completely and without problems. |
| 8 | MAT4 | 50 | App. 1 (comparison) | 320° C.; $3 \times 10^{-5}$ mbar; from liquid phase | Sublimation time: 7 h, purity of sublimate: 96%, decomposition products: 4%. After melting at 220° C., solvent residues from the recrystallisation are liberated. These result in boiling delays and splashing. The condensation surface is contaminated by splashes. After sublimation of about 30 g, the transport of heat away at the condensation surface is so poor that the condensate no longer solidifies and runs back on the flask wall. Due to the high sublimation temperature and time, considerable decomposition occurs, with formation of, inter alia, 4,4'-bis(trimethylsilyl)stilbene, which contaminates the sublimate. |
| 9 | MAT4 | 200 | App. 3 | 240° C.; $2 \times 10^{-3}$ mbar; from liquid phase | Sublimation time: 2 h 20 min, purity of sublimate: 99.5%, decomposition products: none. At 220° C., the material melts. The pressure increases due to liberated residual solvent for 15 min. to $5 \times 10^{-2}$ mbar and then drops back to $5 \times 10^{-5}$ mbar. No boiling delays and thus no splashing occur. The actual sublimation proceeds at 240° C. and with a helium carrier-gas stream |

TABLE 2-continued

Sublimation overview

| No. | Material | Amount used [g] | Sublimer | Sublimation conditions ($T_{oven}$; p; phase; addition) | Observations |
|---|---|---|---|---|---|
| 10 | MAT5 | 50 | App. 1 (comparison) | 330° C.; $5 \times 10^{-5}$ mbar; from the solid phase | which is adjusted so that the pressure remains constant at $8 \times 10^{-4}$ mbar. The sublimation proceeds completely and without problems. The formation of 4,4'-bis(trimethylsilyl)-stilbene is not observed. Sublimation time: 5 h, purity of sublimate: 98.6%, decomposition products: 2.3%. An ash layer forms over time at the glass flask/sublimation material interface. The temperature has to be increased from 330° C. successively to 360° C. in order to ensure an acceptable sublimation rate. Crystals measuring up to several mm form on the surface of the sublimation material. Ash is entrained, which contaminates the sublimate. After sublimation of about 35 g, the sublimation is terminated. |
| 11 | MAT5 | 150 | App. 2 | 330° C.; $5 \times 10^{-5}$ mbar; from the solid phase; addition of 100 g of glass beads (diameter 5 mm) | Sublimation time: 1 h 40 min, purity of sublimate: 99.95%, decomposition products: none. Neither ash nor large crystals form. The sublimation proceeds completely and without problems. |
| 12 | MAT6 | 10 | App. 1 (comparison) | 390° C.; $5 \times 10^{-5}$ mbar; from the solid phase | Sublimation time: 5 h, purity of sublimate: 97.2%, decomposition products: 2.7%. An ash layer forms over time at the glass flask/sublimation material interface. The temperature has to be increased from 390° C. successively to 420° C. in order to ensure an acceptable sublimation rate. Crystals measuring up to several mm form on the surface of the sublimation material. Ash is entrained, which contaminates the sublimate. After sublimation of about 6 g, the sublimation is terminated. The residue consists of an indium-containing ash. |
| 13 | MAT6 | 50 | App. 3 | 350° C.; $7 \times 10^{-4}$ mbar; from the solid phase; addition of 150 g of glass beads (diameter 5 mm) | Sublimation time: 2 h 30 min, purity of sublimate: 99.9%, decomposition products: none. The helium carrier-gas stream is adjusted so that the pressure remains constant at $7 \times 10^{-4}$ mbar. The sublimation proceeds completely and without problems. |

The experiments described show that the substances can be sublimed significantly more quickly, on a larger scale and with considerably less side reaction or decomposition with the process according to the invention. For some of the substances shown above, only the process according to the invention makes sublimation possible at all.

Example 5: Use of the Process According to the Invention for Isomer Separation The partial or complete separation of atropisomers of a compound can be carried out by the process according to the invention, as described below for the atropisomers of 9,10-bis(4-methylnaphth-1-yl)anthracene (WO 06/048268). 100 g of a 1:1 atropisomer mixture of 9,10-bis(4-methylnaphth-1-yl)anthracene are sublimed from the solid phase in apparatus 3 at T=280° C. and p=9×10$^{-4}$ mbar with addition of 200 g of glass beads (diameter 5 mm). After a mass throughput of about 50%, corresponding to 50 g of sublimate and 50 g of residue, the sublimation is terminated. The atropisomer ratio in the sublimate is about 2.3:1.0 with respect to the more readily volatile atropisomer, that of the residue is about 1.0:2.3 with respect to the less volatile isomer. The determination of the atropisomer ratio of the sublimate and of the residue was carried out in accordance with WO 06/048268. By repeated sublimation of the sublimate and termination after a mass throughput of 50% in each case, the more readily volatile atropisomer can be considerably enriched in the sublimate. Ratios of greater than 20:1 can easily be produced in this way. The less volatile atropisomer can be considerably enriched in the residue by mass throughputs of 80% or more. Ratios of greater than 1:20 can easily be produced in this way.

Example 6: Use of the Process According to the Invention for Sublimation on a Large Scale The following examples show that the sublimation by the process according to the invention and in the apparatus according to the invention can also be carried out on a kilogram scale. To this end, the materials employed, the parameters of the sublimation process and the yield and purity after the sublimation are in each case indicated below. The rotation is switched on after the heating.

Example 6a

Material: MAT7 (triarylmonoamine derivative having a molecular weight of about 670 g/mol); purity 99.83%
Filling: 5000 g
Temperature: 285° C.
Final pressure: <10$^{-6}$ mbar
Rotational speed: 1 min$^{-1}$
Duration of the sublimation: 13.5 h
Yield (purity): fraction 1: 4500 g (99.97%), fraction 2: 300 g (99.97%).
A second sublimation increases the purity to >99.99%.

Example 6b

Material: MAT8 (triarylmonoamine derivative having a molecular weight of about 670 g/mol); purity 99.88%
Filling: 5500 g
Temperature: 300° C.
Final pressure: <10$^{-6}$ mbar
Rotational speed: 2 min$^{1}$
Duration: 17 h
Yield (purity): fraction 1: 4690 g (99.99%), fraction 2: 580 g (99.94%).
A second sublimation of fraction 2 increases the purity to >99.99%.

Example 6c

Material: MAT9 (2,4,6-triaryl-1,3,5-triazine derivative having a molecular weight of about 590 g/mol); purity 99.41%
Filling: 5000 g
Temperature: 310° C.
Final pressure: <10$^{-6}$ mbar
Rotational speed: 4 min$^{-1}$
Duration: 13 h
Yield (purity): fraction 1: 4430 g (99.96%), fraction 2: 140 g (99.98%).
A second sublimation increases the purity to >99.99%.

The invention claimed is:

1. Process for the purification of chemical substances which are solid at room temperature (sublimation material), where the substance is heated in vacuo, converted into the gas phase and subsequently condensed, characterised in that the vessel containing the sublimation material and the condensation unit rotate, and in that the process is carried out in an apparatus which has, between the rotating part and the static part, a rotation coupling which is selected from a rotary feedthrough with ferrofluidic seal or a double- or triple-acting mechanical face seal.

2. Process according to claim 1, characterised in that the sublimation material is converted into the gas phase from the solid state or from the melt and in that the condensation takes place into the solid phase or into the liquid phase.

3. Process according to claim 1, characterised in that it is carried out at a pressure of 10$^{-3}$ to 10$^{-7}$ mbar, preferably 10$^{-4}$ to 10$^{-6}$ mbar.

4. Process according to claim 1, characterised in that the sublimation material has a molecular weight in the range from 300 to 5000 g/mol, preferably from 400 to 2500 g/mol, particularly preferably in the range from 450 to 1.500 g/mol.

5. Process according to claim 1, characterised in that the process is carried out using a carrier gas in a pressure range from 10$^{-1}$ to 10$^{-4}$ mbar.

6. Process according to claim 1, characterised in that the process is carried out semi-continuously.

7. Process according to claim 1, characterised in that the rotational speed is in the range from 0.5 to 100 min$^{-1}$, preferably in the range from 1 to 20 min$^{-1}$, particularly preferably in the range from 1.5 to 10 min$^{-1}$.

8. Process according to claim 1, characterised in that the sublimation material is converted into the gas phase at a temperature in the range from 200° C. to 500° C., preferably in the range from 250° C. to 450° C., particularly preferably in the range from 250° C. to 400° C.

* * * * *